United States Patent
Doyle et al.

(10) Patent No.: US 11,771,772 B2
(45) Date of Patent: Oct. 3, 2023

(54) GLYCEMIC CONTROL USING INTRINSIC FACTOR BOUND TO A VITAMIN B$_{12}$ CONJUGATE OF A GLUCAGON-LIKE PEPTIDE-1 RECEPTOR AGONIST

(71) Applicants: Syracuse University, Syracuse, NY (US); Xeragenx LLC, St. Louis, MO (US)

(72) Inventors: Robert Doyle, Manlius, NY (US); Jonathan D. Bortz, St. Louis, MO (US); David S. Hermelin, St. Louis, MO (US)

(73) Assignees: Syracuse University, Syracuse, NY (US); Xeragenx LLC, St. Louis, MO (US)

( * ) Notice: Subject to any disclaimer, the term of this patent is extended or adjusted under 35 U.S.C. 154(b) by 82 days.

(21) Appl. No.: 17/239,934

(22) Filed: Apr. 26, 2021

(65) Prior Publication Data

US 2022/0088203 A1 Mar. 24, 2022

Related U.S. Application Data

(62) Division of application No. 15/575,468, filed as application No. PCT/US2016/033426 on May 20, 2016, now abandoned.

(60) Provisional application No. 62/169,253, filed on Jun. 1, 2015, provisional application No. 62/164,816, filed on May 21, 2015, provisional application No. 62/164,048, filed on May 20, 2015.

(51) Int. Cl.
*A61K 47/55* (2017.01)
*A61K 38/26* (2006.01)
*A61K 38/17* (2006.01)
*A61P 3/10* (2006.01)
*A61K 9/00* (2006.01)

(52) U.S. Cl.
CPC .......... *A61K 47/551* (2017.08); *A61K 9/0019* (2013.01); *A61K 38/17* (2013.01); *A61K 38/26* (2013.01); *A61P 3/10* (2018.01)

(58) Field of Classification Search
CPC ...... A61K 47/551; A61K 38/26; A61K 38/17; A61K 9/0019; A61P 3/10
See application file for complete search history.

(56) References Cited

U.S. PATENT DOCUMENTS

2010/0184642 A1* 7/2010 Berglund ............. A61K 47/551
435/320.1

FOREIGN PATENT DOCUMENTS

WO WO-2008109068 A2 * 9/2008 ......... A61K 38/1709

OTHER PUBLICATIONS

Clardy-James et al, Site-Selective Oxidation of Vitamin B12 Using 2-Iodoxybenzoic Acid, SYNLETT, 2012, 23, pp. 2363-2366.*

* cited by examiner

*Primary Examiner* — Li N Komatsu
(74) *Attorney, Agent, or Firm* — David L. Nocilly

(57) ABSTRACT

The present invention provides compositions and methods for lowering blood glucose. More specifically, the present invention provides compositions comprising a complex comprising IF and B$_{12}$ conjugated to a peptide comprising a GLP-1 agonist. Advantageously, the composition may be delivered subcutaneously.

12 Claims, 5 Drawing Sheets

Specification includes a Sequence Listing.

SEQUENCE LISTING

<160> NUMBER OF SEQ ID NOS: 2

<210> SEQ ID NO 1
<211> LENGTH: 45
<212> TYPE: PRT
<213> ORGANISM: Artificial Sequence
<220> FEATURE:

```
<221> NAME/KEY: MOD_RES
<222> LOCATION: (12)...(12)
<223> OTHER INFORMATION: exendin-4 based peptide from Heloderma
      suspectum with azido group

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Asn Trp Leu Lys Asn Gly Gly Pro
            20                  25                  30

Ser Ser Gly Ala Pro Ser Ser Gly Ala Pro Pro Ser
        35              40              45

<210> SEQ ID NO 2
<211> LENGTH: 45
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Asn Trp Leu Lys Asn Gly Gly Pro
            20                  25                  30

Ser Ser Gly Ala Pro Ser Ser Gly Ala Pro Pro Ser
        35              40              45
```

GLYCEMIC CONTROL USING INTRINSIC FACTOR BOUND TO A VITAMIN $B_{12}$ CONJUGATE OF A GLUCAGON-LIKE PEPTIDE-1 RECEPTOR AGONIST

CROSS-REFERENCE TO RELATED APPLICATIONS

The present application is a divisional of U.S. application Ser. No. 15/575,468, filed on Nov. 20, 2017, currently abandoned, which was a national stage of PCT/US16/33426, filed on May 20, 2016, and which claimed priority to U.S. Provisional Application No. 62/164,048, filed on May 20, 2015.

FIELD OF THE INVENTION

The present invention encompasses compositions and methods for lowering blood glucose. More specifically, the present invention provides compositions comprising a complex comprising IF and $B_{12}$ conjugated to a peptide comprising a GLP-1 receptor agonist. Advantageously, the composition may be delivered subcutaneously.

BACKGROUND OF THE INVENTION

Diabetes mellitus (DM) is a chronic metabolic disorder caused by an absolute or relative deficiency of insulin hormone. Insulin is produced by the beta cells of the islets of Langerhans located in the pancreas, and the absence, destruction, or other loss of these cells results in type 1 DM, or insulin-dependent diabetes mellitus (IDDM). Most children with diabetes have IDDM and a lifetime dependence on regular injections of exogenous insulin. Overall incidence is at least 15 cases per 100,000 individuals annually and probably increasing. An estimated 3 children out of 1000 develop IDDM by age 20 years. More than 700,000 Americans have type 1 DM.

Type 2 DM, or non-insulin-dependent diabetes mellitus (NIDDM) is a heterogeneous disorder. Most patients with NIDDM have insulin resistance, and their beta cells lack the ability to overcome this resistance. Although this form of diabetes was previously uncommon in children, in some, countries 20% or more of new patients with diabetes in childhood and adolescence have NIDDM, a change associated with increased rates of obesity. Other patients may have inherited disorders of insulin release leading to maturity onset diabetes of the young (MODY). Of the total incidence of diabetes in the U.S., NIDDM accounts for about 90%, whereas IDDM accounts for the remaining 10%.

Glucagon-like peptide-1 (GLP-1) is cleaved from preproglucagon as a 36- or 37-amino acid molecule within the intestine, where it is co-localized in the endocrine L-cells of the distal gut with PYY. The peptide mediates glucose-dependent insulinotropic effects in a number of species, including man. GLP-1(7-36)amide also inhibits gastric acid secretion and gastric emptying, as well as suppressing glucagon release (therefore reducing hepatic-derived glucose) and promoting an increase in pancreatic β-cell mass. As a therapeutic target, there has been substantial interest in GLP-1, since actions of GLP-1 (inhibition of gastric emptying; decreased blood glucose concentration) are preserved in subjects with poorly controlled Type 2 Diabetes. Although agonists for the GLP-1 receptor are available, there is a need in the art for GLP-1 receptor agonists with improved efficacy and pharmacokinetics.

DETAILED DESCRIPTION OF THE INVENTION

The present invention comprises the use of intrinsic factor to enhance the efficacy of a peptide comprising a glucagon-like peptide-1 (GLP-1) receptor agonist following administration. A peptide of interest is conjugated to $B_{12}$ (or a $B_{12}$ analog) and the $B_{12}$ conjugate is then complexed with intrinsic factor. Such a composition is suitable for subcutaneous administration and shows enhanced activity at lowering blood glucose relative to a composition that doesn't comprise intrinsic factor. Accordingly, the invention provides a method of lowering blood glucose following administration of a pharmaceutical composition comprising a complex comprising IF and a $B_{12}$ conjugate, wherein the $B_{12}$ is conjugated to a peptide comprising a GLP-1 receptor agonist. The pharmaceutical compositions disclosed herein enable a rapid and significant drop in glucose levels following administration.

I. Composition

The present invention encompasses a pharmaceutical composition comprising intrinsic factor and $B_{12}$ or an analog thereof, wherein the $B_{12}$ or analog thereof is conjugated to a peptide comprising a glucagon-like peptide-1 (GLP-1) receptor agonist. $B_{12}$ analogs may be modified to improve conjugation chemistry, bioavailability, solubility, stability, handling properties, or a combination thereof, as compared to an unmodified version of $B_{12}$. Thus, in another aspect, a composition of the invention comprises a modified $B_{12}$ or B$_{12}$ analog. In still another aspect, a composition of the invention comprises a prodrug of B$_{12}$ or a B$_{12}$ analog.

A composition of the invention may further comprise a pharmaceutically acceptable excipient, carrier or diluent. Further, a composition of the invention may contain preserving agents, solubilizing agents, stabilizing agents, salts (substances of the present invention may themselves be provided in the form of a pharmaceutically acceptable salt), buffers, or antioxidants.

(a) Vitamin B$_{12}$ (Cobalamin)

Vitamin B$_{12}$ is a water-soluble vitamin with a highly complex structure, comprising a midplanar corrin ring composed of four pyrroline elements linked to a central cobalt (III) atom. Throughout the disclosure vitamin B$_{12}$, B$_{12}$ and cobalamin may be used interchangeably.

Figure 1:
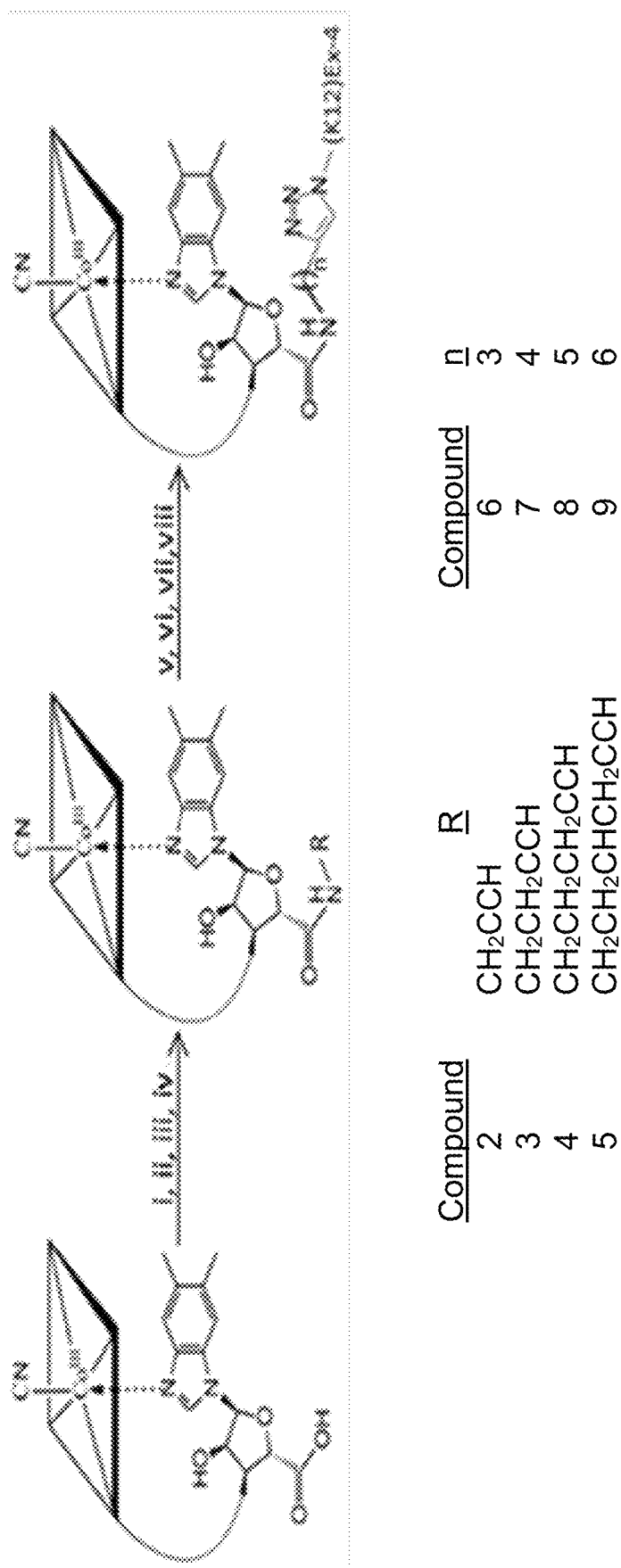
FIG. 1 depicts the structure of Vitamin $B_{12}$ showing the Co (III) atom coordinated by the four nitrogens of the corrin ring, dimethylbenzimidazole (DMB), and the X group which can be a cyanide, methyl, or deoxyadenosyl groups and a schematic of the synthesis of $B_{12}$-Ex-4 conjugates with the following reagents and conditions: (i) EDCl, HOBt, propargyl amine, rt, DMSO, 16 h; (ii) EDCl, HOBt, 1-amino-3-butyne, rt, DMSO, 16 h; (iii) EDCl, HOBt, 1-amino-4-pentyne, rt, DMSO, 16 h; (iv) EDCl, HOBt, 1-amino-5-hexyne, rt, DMSO, 16 h; (v) (2), $CuSO_4$, sodium ascorbate, 1, Water/DMF 4:1, 1 h; (vi) (3), $CuSO_4$, sodium ascorbate, 1, Water/DMF 4:1, 1 h; (vii) (4), $CuSO_4$, sodium ascorbate, 1, Water/DMF, 4:11 h; (viii) (5), $CuSO_4$, sodium ascorbate, 1, 1 h.

In the structure of vitamin B$_{12}$, the central cobalt(III) atom is six-coordinated, with the equatorial positions filled by the nitrogen atoms of the corrin macrocycle. The (conventionally) 'lower', 'α'-axial site is occupied by an imidazole nitrogen atom from a 5',6'-dimethylbenzimidazole (DMB) base whereas the 'upper', 'β'-axial site can be occupied by various X groups (e.g. CN$^-$, CH$_3^-$, Ado$^-$, SCN$^-$, SeCN$^-$, SO$_3^-$ and thiourea). The corrin ring incorporates seven amide side chains, three acetamides (a, c, g) and four propionamides (b, d, e, f). The four pyrrole rings are usually indicated as A, B, C and D, as shown in FIG. 1.

Several functional groups are readily available for modification and/or conjugation on B$_{12}$, including propionamides, acetamides, hydroxyl groups, the cobalt(III) ion and the phosphate moiety. As used herein, a modification of B$_{12}$ may be any modification on B$_{12}$ that improves conjugation chemistry, bioavailability, solubility, stability, handling properties, or a combination thereof. As used herein, conjugation of B$_{12}$ describes the conjugation of a peptide to B$_{12}$ or modified B$_{12}$. Accordingly, a B$_{12}$ conjugate of the invention may be modified and/or conjugated at a propionamide, acetamide, hydroxyl group, the cobalt(III) ion and the phosphate moiety, provided the B$_{12}$ conjugate binds IF. Non-limiting examples of modification or conjugation sites for a B$_{12}$ conjugate of the invention include at the a-position or b-position on the A-ring, at the c-position or d-position on the B-ring, at the e-position on the C-ring, at the g-position on the D ring, at the f-position, at the phosphate moiety, at the 5'- or 2'-hydroxyl on the ribose, and at the cobalt ion. Preferred sites of modification and/or conjugation may include sites on the A ring such as the b-position, sites on the C ring such as the e-position, sites on the ribose unit such as the 5'-hydroxyl group, and the cobalt cation. Specifically, the e-position may be modified and/or conjugated to allow interaction with IF. However, other sites of modification and/or conjugation may be utilized provided they maintain the binding affinity of B$_{12}$ for IF. In a specific embodiment, the 5'-hydroxyl on the ribose may be modified to a carboxylic acid. The resulting carboxylic acid may then be used to conjugate B$_{12}$ to a peptide. A method of performing this is described in more detail below and in the Examples.

Methods for modification and/or conjugation to B$_{12}$ are known in the art. The following provides non-limiting examples of methods for modification and/or conjugation. It is contemplated that various other methods for modification and/or conjugation common in the art of synthetic chemistry may be used. For example, carefully controlled partial hydrolysis of cyanocobalamin under acidic conditions gives access to desirable b and e acids. Methods for 5'-OH functionalization may rely on the reaction of cyanocobalamin ((CN)Cbl) with anhydrides, furnishing unstable ethers. Another method for conjugation may be the carbamate or carbonate methodology as described by Russell-Jones (WO 1999/065390, which is hereby incorporated by reference in its entirety). Briefly, the hydroxyl group at position 5' is first reacted with a carbonyl group equivalent—1,1'-carbonyldiimidazole (CDI) or 1,1'-carbonylbis(1,2,4-triazole) (CDT)—and then treated with an amine or an alcohol giving carbamates and carbonates, respectively, at the 5'-position of the ribose tail. Alternatively, the 5'-OH group can be oxidized to the corresponding carboxylic acid using the 2-iodoxybenzoic acid (IBX)/2-hydroxypyridine (HYP) system as an oxidant and then coupled with amines. Another effective approach may rely on [1,3] dipolar cycloaddition. The 5'-OH is transformed into a good leaving group and subsequently substituted with an azide. The resulting "clickable" azide is stable and highly active in the copper-catalyzed as well as in the strain promoted [1,3] dipolar cycloaddition (CuAAC or SPAAC) to alkynes. This methodology is described in detail in Chrominski et al, *Chem Eur J* 2013; 19: 5141-5148, which is hereby incorporated by reference in its entirety. In a specific embodiment, the 5'-OH is oxidized to a carboxylic acid. An alkyne is then added to the carboxylic acid. A peptide may then be conjugated to B$_{12}$ via the alkyne group.

Functionalization of the cobalt ion may be accomplished by either alkylation or utilization of cyanide ligand properties to act as an electron pair donor for transition metals, resulting in bimetallic complexes. The synthesis of organometallic species requires reduction of the cobalt(III) to cobalt(I) B$_{12}$ and its subsequent reaction with electrophiles: alkyl halides, acyl halides, Michael acceptors, epoxides, etc. Alternatively, reduction may not be required and instead, the direct reaction of (CN)Cbl with terminal alkynes in the presence of Cu(I) salts may furnish acetylides in excellent yields. This methodology may allow the conjugation of two moieties to B$_{12}$ and is described in further detail in Chrominski et al, *J Org Chem* 2014; 79: 7532-7542, which is hereby incorporated by reference in its entirety. Accordingly, it is contemplated that two peptides may be conjugated to B$_{12}$. Briefly, using this methodology, "doubly clickable" vitamin B$_{12}$, a valuable building block for further functionalization via [1,3] dipolar azide-alkyne cycloaddition, may be prepared. A combination of AAC (CuAAC and SPAAC) with the carbamate method may allow conjugation at both the central cobalt ion and the 5'-position.

B$_{12}$ or an analog thereof and a peptide may be: i) conjugated directly together; or ii) held apart by a 'linker' to produce distance between the B$_{12}$ or an analog thereof and the peptide. The peptide is described in more detail in Section I(b). In an embodiment, B$_{12}$ or an analog thereof may be conjugated to a peptide directly. In another embodiment, an intervening amino acid sequence or linker can be used to conjugate the peptide to B$_{12}$. It is to be understood that conjugation of the B$_{12}$ or an analog thereof to a peptide will not adversely affect either the binding function of the B$_{12}$ or an analog thereof to IF or the function of the peptide. Suitable linkers include, but are not limited to, amino acid chains and alkyl chains functionalized with reactive groups for conjugating to both the B$_{12}$ or analog thereof and the peptide.

In an embodiment, the linker may include amino acid side chains, referred to as a peptide linker. Accordingly, amino acid residues may be added to B$_{12}$ or an analog thereof for the purpose of providing a linker by which B$_{12}$ or an analog thereof can be conveniently affixed to a peptide. Amino acid residue linkers are usually at least one residue and can be 40 or more residues, more often 1 to 10 residues. Typical amino acid residues used for linking are tyrosine, cysteine, lysine, glutamic and aspartic acid, or the like.

In another embodiment, the linker may be an alkyl chain linking group. For example, by reacting an amino group of $B_{12}$ or an analog thereof with a first functional group on the alkyl chain, such as a carboxyl group or an activated ester. Subsequently a peptide may be attached to the alkyl chain to complete the formation of a conjugate by reacting a second functional group on the alkyl chain with an appropriate group on the peptide. The second functional group on the alkyl chain is selected from substituents that are reactive with a functional group on the peptide while not being reactive with $B_{12}$ or an analog thereof. For example, when the peptide incorporates a functional group, such as a carboxyl group or an activated ester, the second functional group of the alkyl chain linking group can be an amino group. Alternatively, by reacting a carboxylic acid group generated from the oxidation of the 5'-hydroxyl of the ribose on $B_{12}$, with a bifunctional amine-alkyne of variable methylene spacer length, a $B_{12}$-alkyne compound may be generated. Subsequently, a peptide may be attached to the alkyl chain to complete the formation of the conjugate by reaction a second functional group on the alkyl chain with an appropriate group on the peptide. In the aforementioned embodiment, the second functional group on the alkyl chain is an alkyne. A peptide modified with a functional group that reacts with an alkyne may then be conjugated to the alkyl chain. For example, a peptide modified with an azido group may be conjugated to the alkyne group on the alkyl chain.

It will be appreciated that formation of the conjugate may require protection and deprotection of the functional groups present in order to avoid formation of undesired products. Protection and deprotection are accomplished using protecting groups, reagents, and protocols common in the art of organic synthesis. It will be appreciated that linking groups may alternatively be coupled first to the peptide and then to $B_{12}$ or an analog thereof. An alkyl chain linking group may be one to 40 or more atoms long, more often 1 to 10 atoms long. Additionally, an alkyl chain linking group may comprise one or more heteroatoms (e.g. O, N, S). In certain embodiments, an alkyl chain linking group may be 1, 2, 3, 4, 5, 6 or 7 atoms long. In a specific embodiment, an alkyl chain linking group may comprise 3, 4, 5, or 6 carbons. In another specific embodiment, an alkyl chain linking group may comprise 4 carbons.

An alternative chemical linking group to an alkyl chain is polyethylene glycol (PEG), which is functionalized in the same manner as the alkyl chain described above for incorporation in the conjugates. $B_{12}$ or an analog thereof may be PEGylated for improved systemic half-life and reduced dosage frequency. In an embodiment, PEG may be added to a linker. As such, $B_{12}$ or an analog thereof may comprise a linker and PEG.

(b) Peptide

In an aspect, $B_{12}$ or an analog thereof may be conjugated to a peptide comprising a glucagon-like peptide-1 (GLP-1) receptor agonist. By "peptide" is meant an amino acid sequence that includes 5 or more amino acid residues. "Peptide" refers to both short chains, commonly referred to as peptides, oligopeptides, or oligomers, and to longer chains, up to about 100 residues in length. A peptide may comprise about 5 or more amino acids. For example, a peptide may comprise about 5 or more, about 10 or more, about 15 or more, about 20 or more, about 25 or more, about 30 or more, about 35 or more, about 40 or more, about 45 or more, about 50 or more, about 55 or more, about 60 or more, about 65 or more, about 70 or more, about 75 or more, about 80 or more, about 85 or more, about 90 or more, about 95 or more, or about 100 or more amino acids. In certain embodiments, a peptide may comprise 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 amino acids. In other embodiments, a peptide may comprise from about 30 to about 60 amino acids. In still other embodiments, a peptide may comprise from about 35 to about 55 amino acids. In yet other embodiments, a peptide may comprise from about 40 to about 55 amino acids. In a specific embodiment, a peptide may comprise about 45 amino acids. In an exemplary embodiment, a peptide comprises 45 amino acids.

A peptide may be ordered (α-helix or β-sheet), disordered, or a combination thereof. In certain embodiments, a peptide may adopt an α-helical structure. In other embodiments, a peptide may adopt an α-helical structure with a disordered terminal end.

A peptide may comprise a glucagon-like peptide-1 (GLP-1) receptor agonist. A GLP-1 receptor agonist may also be referred to as an incretin mimetic. GLP-1 is an incretin derived from the transcription product of the proglucagon gene. The biologically active forms of GLP-1 are: GLP-1-(7-37) and GLP-1-(7-36)$NH_2$. A GLP-1 receptor agonist interacts with and is an agonist of the GLP-1 receptor and may be used for the treatment of type 2 diabetes. Any suitable GLP-1 receptor agonist may be used in the invention. Non-limiting examples of GLP-1 receptor agonists may include exendin-4 (EX-4), exenatide (BYETTA/BYDUREON), liraglutide (VICTOZA, SAXENDA), lixisenatide (LYXUMIA), albiglutide (TANZEUM), dulaglutide (TRULICITY), and taspoglutide. In certain embodiments, a GLP-1 receptor agonist may be an exendin-4 (EX-4) peptide. In a specific embodiment, a GLP-1 receptor agonist may comprise the sequence set forth in SEQ ID NO:2 (HGEGTFTSDLSKQMEEE-AVRLFIENWLKNGGPSSGAPSSGAPPPS). Alternatively, a GLP-1 receptor agonist of the invention may be modified to facilitate conjugation to $B_{12}$. For example, a GLP-1 receptor agonist may comprise the sequence set forth in SEQ ID NO:1 (HGEGTFTSDLS(Kazido)QMEEE-AVRLFIENWLKNGGPSSGAPSSGAPPPS), wherein the lysine at the 12 position is modified with an azido group.

A peptide of the invention may be subject to various changes, substitutions, insertions, and deletions where such changes provide for certain advantages in its use. Thus, the invention encompasses any of a variety of forms of peptide derivatives that include amides, cyclized peptides, polymerized peptides, conservatively substituted variants, analogs, fragments, peptoids, chemically modified peptides, and peptide mimetics. In addition, a peptide can be modified by terminal-$NH_2$ acylation (e.g., acetylation, or thioglycolic acid amidation) or by terminal-carboxylamidation (e.g., with ammonia, methylamine, and the like terminal modifications)

Peptides of the invention may comprise naturally occurring amino acids, synthetic amino acids, genetically encoded amino acids, non-genetically encoded amino acids, and combinations thereof. Peptides may include both L-form and D-form amino acids.

Representative non-genetically encoded amino acids may include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids may include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence similar to a sequence of a reference peptide in which one or more residues have been conservatively substituted with a functionally similar residue and which displays the same or similar targeting activity. The phrase "conservatively substituted variant" also includes peptides wherein a residue is replaced with a chemically derivatized residue, provided that the resulting peptide displays targeting activity.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the present invention, including peptoids, may be synthesized by any of the techniques that are known to those skilled in the art of peptide synthesis. Synthetic chemistry techniques, such as a solid-phase Merrifield-type synthesis, may be preferred for reasons of purity, antigenic specificity, freedom from undesired side products, ease of production and the like. A summary of representative techniques can be found in Stewart & Young (1969) Solid Phase Peptide Synthesis. Freeman, San Francisco; Merrifield (1969) Adv Enzymol Relat Areas Mol Biol 32:221-296; Fields & Noble (1990) Int J Pept Protein Res 35:161-214; and Bodanszky (1993) Principles of Peptide Synthesis. 2nd rev. ed. Springer-Verlag, Berlin; New York. Solid phase synthesis techniques can be found in Andersson et al. (2000) Biopolymers 55:227-250, references cited therein, and in U.S. Pat. Nos. 6,015,561, 6,015,881, 6,031,071, and 4,244,946. Peptide synthesis in solution is described by Schröder & Lübke (1965) The Peptides. Academic Press, New York. Appropriate protective groups usable in such synthesis are described in the above texts and in McOmie (1973) Protective Groups in Organic Chemistry. Plenum Press, London, New York. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif. and PeptidoGenics of Livermore, Calif.).

(c) Intrinsic Factor

In an aspect, IF is bound to a $B_{12}$ conjugate of the invention thereby forming a complex. As used herein, a complex of the invention comprises IF complexed to a $B_{12}$ conjugate of the invention. Intrinsic factor (IF) is a glycosylated protein that is secreted from the gastric mucosa and the pancreas. IF binds $B_{12}$ with picomolar affinity ($K_d$~1 pM). In the $B_{12}$ uptake pathway, the IF protein facilitates transport of $B_{12}$ across the intestinal enterocyte, which occurs by receptor-mediated endocytosis at the apically expressed IF-$B_{12}$ receptor (cubilin). Cubilin works to transport $B_{12}$ in concert with an anchoring protein amnionless (Am). Following transcytosis, and between 2.5 and 4 h after initial ingestion, $B_{12}$ appears in blood plasma bound to the third trafficking protein, transcobalamin II (TCII). The inventors have discovered that conjugating a peptide comprising a glucagon-like peptide-1 (GLP-1) receptor agonist to $B_{12}$ which is then complexed with IF, enables a rapid and significant drop in glucose levels following subcutaneous administration. This is in contrast to the same peptide that when administered conjugated to $B_{12}$ demonstrated no activity following subcutaneous administration.

The IF may be complexed to $B_{12}$ before or after conjugation of $B_{12}$ or an analog thereof to a peptide. In a specific embodiment, IF may be complexed to $B_{12}$ or an analog thereof after conjugation of $B_{12}$ or an analog thereof to a peptide. In an embodiment, IF may be pre-complexed to a $B_{12}$ conjugate by combining the conjugate with IF in solution. By way of non-limiting example, $B_{12}$ conjugate may be combined with IF in PBS at pH 7.4 or in MES buffer at pH 5.5 or in water at pH 8 at temperatures ranging from about 25° C. to about 37° C. For binding, IF may be contacted with $B_{12}$ conjugate for at least 30 minutes. Alternatively, IF may be contacted with $B_{12}$ conjugate for at least 5 min, at least 10 min, at least 15 minutes, at least 20 min, at least 30 minutes, at least 45 minutes, at least 1 hour, at least 2 hours, at least 3 hours, at least 4 hours, at least 5 hours or at least 6 hours. A skilled artisan would be able to determine the various conditions upon which IF and $B_{12}$ conjugate may be pre-complexed.

For pre-complexing of IF and the $B_{12}$ conjugate, IF and the $B_{12}$ conjugate may be combined in solution. One IF complexes with one $B_{12}$ conjugate. Accordingly, the ratio of IF to $B_{12}$ conjugate added to solution may be 1:1. However, to facilitate saturation of the IF with $B_{12}$ conjugate, a greater amount of IF may be added to solution relative to $B_{12}$ conjugate. For example, the ratio of IF to $B_{12}$ conjugate may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, or 100:1. In specific embodiments, the ratio of IF to $B_{12}$ conjugate may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, or 10:1. In other embodiments, an excess of 5% or more IF relative to $B_{12}$ conjugate may be added to solution. For example, an excess of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90% or 100% IF relative to $B_{12}$ conjugate may be added to solution. In specific embodiments, an excess of 5%, 6%, 7%, 8%, 9%, 10%, 11%, 12%, 13%, 14%, or 15% IF relative to $B_{12}$ conjugate may be added to solution. Preferably, in some embodiments, excess IF is added to the solution relative to $B_{12}$ conjugate. However, it may be necessary to add a greater amount of $B_{12}$ conjugate relative to IF to reduce or eliminate un-complexed IF. Accordingly, the ratio of $B_{12}$ conjugate to IF may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, or 100:1. In specific embodiments, the ratio of $B_{12}$ conjugate to IF may be 1.1:1, 1.2:1, 1.3:1, 1.4:1, 1.5:1, 2:1, 2.5:1, 3:1, 3.5:1, 4:1, 4.5:1, 5:1, 6:1, 7:1, 8:1, 9:1, or 10:1. In other embodiments, an excess of 5% or more $B_{12}$ conjugate relative to IF may be added to solution. For example, an excess of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90% or 100% $B_{12}$ conjugate relative to IF may be added to a solution. In a specific embodiment, an excess of 5%, 6%, 7%, 8%, 9%, 10%, 11%, 12%, 13%, 14%, or 15% $B_{12}$ conjugate relative to IF may be added to a solution. Prior to administration of a composition of the invention, it may be necessary to remove un-complexed IF and/or un-complexed $B_{12}$ conjugate.

IF of the invention may be expressed and purified via standard methodology. In a preferred embodiment, IF of the invention is in a pharmaceutically acceptable form. As used in this context, "pharmaceutically acceptable" means the IF is expressed in an environment that is not contaminated with other $B_{12}$ binding proteins or B12 analogs, is extracted in an environment that is not contaminated with other $B_{12}$ binding proteins, and is scalable and reproducible per applicable regulatory standards. IF may be expressed and purified from a transgenic plant, such as *Arabidopsis*. For example, see US 2010/0184642, which is hereby incorporated by reference in its entirety. The expressed and purified IF may be from any species, provided it binds to $B_{12}$ and human cubilin. A skilled artisan will appreciate that IF can be found in a variety of species. Non-limiting examples include human (NP_005133.2), mouse (P52787.2), rat (NP_058858.1), dog (Q5XWD5.1), cat (XP_003993466.1), cattle (NP_001193168.1), non-human primates (EHH56203.1, XP_004051305.1), and horse (XP_008508117.1). It is appreciated that the present invention is directed to homologs of IF in other organisms and is not limited to the human protein. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See National Center for Bioechnology Information, National Institutes of Health for more details. In some embodiments, a homolog has at least 80%, at least 81%, at least 82%, at least 83%, at least 84%, at least 85%, at least 86%, at least 87%, at least 88%, or 89% identity to human IF. In another embodiment %, a homolog has at least 90%, at least 91 at least %, at least 92 at least %, at least 93 at least %, at least 94%, at least 95%, at least 96%, at least 97%, at least 98%, at least 99%, or at least 100% identity to human IF. For instance, a homolog may have at least 80%, at least 81%, at least 82%, at least 83%, at least 84%, at least 85%, at least 86%, at least 87%, at least 88%, or 89% identity to human IF. In another embodiment %, a homolog has at least 90%, at least 91 at least %, at least 92 at least %, at least 93 at least %, at least 94%, at least 95%, at least 96%, at least 97%, at least 98%, at least 99%, or at least 100% identity to the IF sequence accession number NP_005133.2.

In a specific embodiment, the IF comprises the sequence disclosed in accession number NP_005133.2. In other embodiments, the IF comprises the sequence disclosed in accession number NP_005133.2 but for one to 10 conservative amino acid substitutions. For example, the IF comprises the sequence disclosed in accession number NP_005133.2 but for 1, 2, 3, 4, 5, 6, 7, 8, 9 or 10 conservative amino acid substitutions. As used herein, a "conservative amino acid substitution" is one in which the amino acid residue is replaces with an amino acid residue having a similar side chain. Families of amino acid residues having similar side chains have been defined in the art. These families include amino acids with basic side chains (e.g. lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g. glycine, alanine, valine, leucine, isoleucine, proline, phenylalanine, methionine, tryptophan, histidine). The resulting peptide comprising the substitution should have similar characteristics or properties including size, hydrophobicity, etc., such that the overall functionally of the peptide does not significantly change. As the structure of IF bound to $B_{12}$ is known in the art, a skilled artisan would be able to determine amino acids essential to $B_{12}$ binding to ensure binding to $B_{12}$ or a $B_{12}$ conjugate.

(d) Pharmaceutical Composition

The present disclosure also provides pharmaceutical compositions. The pharmaceutical composition comprises a complex of intrinsic factor and a $B_{12}$ conjugate, as an active ingredient, and at least one pharmaceutically acceptable excipient. In a specific embodiment, the compositions may be formulated for subcutaneous or intraperitoneal administration. Compositions for subcutaneous or intraperitoneal administration are generally in the form of a liquid.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered parenterally (i.e. subcutaneous and intraperitoneal) in dosage unit formulations containing conventional nontoxic pharmaceutically acceptable carriers, adjuvants, and vehicles as desired. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980). In a specific embodiment, a composition may be an oral composition.

For parenteral administration (including subcutaneous and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. For additional information regarding intraperitoneal administration, see de Vin et al., Peritoneal Dialysis International 2009; 29: 5-15.

The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

In certain embodiments, a composition comprising a complex of intrinisic factor and a $B_{12}$ conjugate is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a complex of intrinsic factor and a $B_{12}$ conjugate in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a complex of intrinsic factor and a $B_{12}$ conjugate may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a complex of intrinsic factor and a $B_{12}$ conjugate (i.e., having at least one methionine compound) may be prepared by any known method of preparing liposomes for drug delivery, such as, for example, detailed in U.S. Pat. Nos. 4,241,046, 4,394,448, 4,529,561, 4,755, 388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A complex of intrinsic factor and a $B_{12}$ conjugate may be encapsulated in a microemulsion by any method generally known in the art.

In yet another embodiment, a complex of intrinsic factor and a $B_{12}$ conjugate may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

In an aspect, a composition of the invention may be used in a method to lower blood glucose in a subject. The method comprises administering an effective amount of a pharmaceutical composition comprising intrinsic factor complexed with $B_{12}$ or an analog thereof, wherein the $B_{12}$ or analog thereof is conjugated to a peptide comprising a glucagon-like peptide-1 (GLP-1) receptor agonist. In certain embodiments, the composition may be administered subcutaneously or intraperitoneally.

In another aspect, a composition of the invention may be used in a method for treating diabetes mellitus in a subject. The method comprises administering to the subject an effective amount of a pharmaceutical composition comprising intrinsic factor complexed with $B_{12}$ or an analog thereof, wherein the $B_{12}$ or analog thereof is conjugated to a peptide comprising a glucagon-like peptide-1 (GLP-1) receptor agonist. In certain embodiments, the composition may be administered subcutaneously or intraperitoneally. Diabetes mellitus (DM) is a chronic metabolic disorder caused by an absolute or relative deficiency of insulin hormone. Insulin is produced by the beta cells of the islets of Langerhans located in the pancreas, and the absence, destruction, or other loss of these cells results in type 1 DM, or insulin-dependent diabetes mellitus (IDDM). Type 2 DM, or non-insulin-dependent diabetes mellitus (NIDDM) is a heterogeneous disorder. Most patients with NIDDM have insulin resistance, and their beta cells lack the ability to overcome this resistance.

By lowering blood glucose is meant that blood glucose is lowered by more than 1-fold relative to no treatment. For example, blood glucose is lowered by more than 1-fold, more than 1.5-fold, more than 2-fold, more than 2.5-fold, more than 3-fold, more than 3.5-fold, more than 4-fold, more than 4.5-fold or more than 5-fold relative to no treatment. In certain embodiments, blood glucose is lowered by more than 1-fold, more than 1.1-fold, more than 1.2-fold, more than 1.3-fold, more than 1.4-fold, more than 1.5-fold, more than 1.6 fold, more than 1.7-fold, more than 1.8-fold, more than 1.9-fold or more than 2-fold relative to no treatment.

Using a method of the invention, lowering of blood glucose by administering a peptide within a complex is increased relative to a peptide alone or a peptide conjugated to $B_{12}$. Accordingly, a peptide within a complex may lower blood glucose by more than 1-fold relative to a peptide conjugated to $B_{12}$. For example, a peptide within a complex may lower blood glucose by more than 1-fold, more than 1.5-fold, more than 2-fold, more than 2.5-fold, more than 3-fold, more than 3.5-fold, more than 4-fold, more than 4.5-fold or more than 5-fold relative to a peptide conjugated to $B_{12}$. In certain embodiments a peptide within a complex may lower blood glucose by more 1-fold, more than 1.1-fold, more than 1.2-fold, more than 1.3-fold, more than 1.4-fold, more than 1.5-fold, more than 1.6 fold, more than 1.7-fold, more than 1.8-fold, more than 1.9-fold or more than 2-fold relative to a peptide conjugated to $B_{12}$.

The bioavailability of GLP-1 receptor agonists following subcutaneous administration is generally poor. There is a need to develop GLP-1 receptor agonists with increased bioavailability to enhance their use in the treatment of diabetes. Advantageously, the methods disclosed herein provide a means to subcutaneously deliver a GLP-1 receptor agonist that enables a rapid and significant drop in glucose levels. The complex comprising IF and $B_{12}$ conjugated to a peptide comprising a GLP-1 receptor agonist increases the bioavailability of the peptide relative to peptide conjugated to $B_{12}$. Accordingly, the bioavailability of the peptide conjugated to $B_{12}$ and complexed with IF is increased relative to a peptide conjugated to $B_{12}$.

In certain embodiments, a method of the invention encompasses a method of mitigating the effect of TCII sequestration of a $B_{12}$ conjugate, after administration of the conjugate to a subject. The method comprises complexing the $B_{12}$ conjugate with IF before administering the complex to the subject. Suitable $B_{12}$ conjugates include $B_{12}$-peptide conjugates as described above, and also may include $B_{12}$-small molecule conjugates. Importantly, such $B_{12}$-small molecule conjugates must (a) maintain biological activity of the small molecule, and (b) maintain binding of the conjugate to IF. Suitable $B_{12}$-small molecule conjugates are known in the art. A complex of the present method may be administered subcutaneously, intraperitoneally, or another parental administration route.

A method of the invention may be used lower blood glucose in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In certain embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

As used herein, the term "effective amount" means an amount of a peptide that leads to measurable and beneficial effects for the subject administered the substance. The effective amount or dose of peptide administered according to this discovery will be determined by the circumstances surrounding the case, including the peptide administered, the status of the symptoms being treated, the medical history of the subject as well as other considerations known by a skilled artisan.

Determination and adjustment of a therapeutically effective dose, as well as evaluation of when and how to make such adjustments, are known to those of ordinary skill in the art of medicine. In some embodiments, a minimal dose is administered, and dose is escalated in the absence of dose-limiting toxicity. One of skill in the art will be able to determine the therapeutically effective dose.

A composition of the disclosure may be administered as multiple doses. Administration may be daily, twice-daily, three times per day, weekly, twice weekly, monthly, twice monthly, or more. The duration of treatment can and will vary depending on the subject and disease to be treated. For example, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Synthesis of $B_{12}$ Precursors (Compounds 2-5) and Ex-4 (Compound 1) Conjugates (Compounds 6-9)

Synthesis was conducted in three stages as seen in FIG. 1. First, the 5'-hydroxyl group of $B_{12}$ was converted to a carboxylic acid using 2-iodoxybenzoic acid. The second step required reaction with a bifunctional amine-alkyne of variable methylene (n) spacer length (n=1-4). The third step involved reaction of the final '$B_{12}$-alkyne' compound with Ex-4 modified at the lysine 12 (K12) position with an ε-azido group (compound 1).

Synthesis of compound 3 using 1-amino-3-butyne as the bifunctional linker has been reported. The present invention used the latter chemistry, modified for the synthesis of compounds 2, 4, and 5, through use of either propargylamine (compound 2), 1-amino-4-pentyne (compound 4), or 1-amino-5-hexyne (compound 5), respectively. Briefly, the $B_{12}$ modified 5'-carboxylic acid was reacted with each linker in the presence of 1-ethyl-3-[3-dimethylaminopropyl]carbodiimide hydrochloride (EDCl) and hydroxybenzotriazole (HOBt) in dry DMSO at room temperature overnight, with greater than 95% isolated yields in all cases, as seen in FIG. 1.

Compound 1 was then conjugated to $B_{12}$ using copper-catalyzed alkyne-azide cycloaddition (CuAAC). This conjugation was achieved by dissolving compound 1 with either compounds 2-5, respectively with copper (II) sulfate and sodium ascorbate in water/DMF (4:1) and stirring for 1 h. The reaction yields were greater than 90% with isolated purity greater than 95% for compounds 6-9 as indicated by HPLC in all cases, as seen in FIG. 1 and FIG. 2.

Example 2. Purification and Characterization of 2-5 and 6-9

Compounds 2-5 were purified by RP-HPLC using a C18 column monitoring at 360 nm. A mobile phase of 0.1% TFA water was used with a flow rate of 1 mL/min and a gradient of 0-13% acetonitrile over 13 minutes. Compounds 2-5 were then characterized by $^1H$ NMR and matrix-assisted laser desorption ionization time-of-flight mass spectrometry (MALDI-Tof MS).

Figure 2:
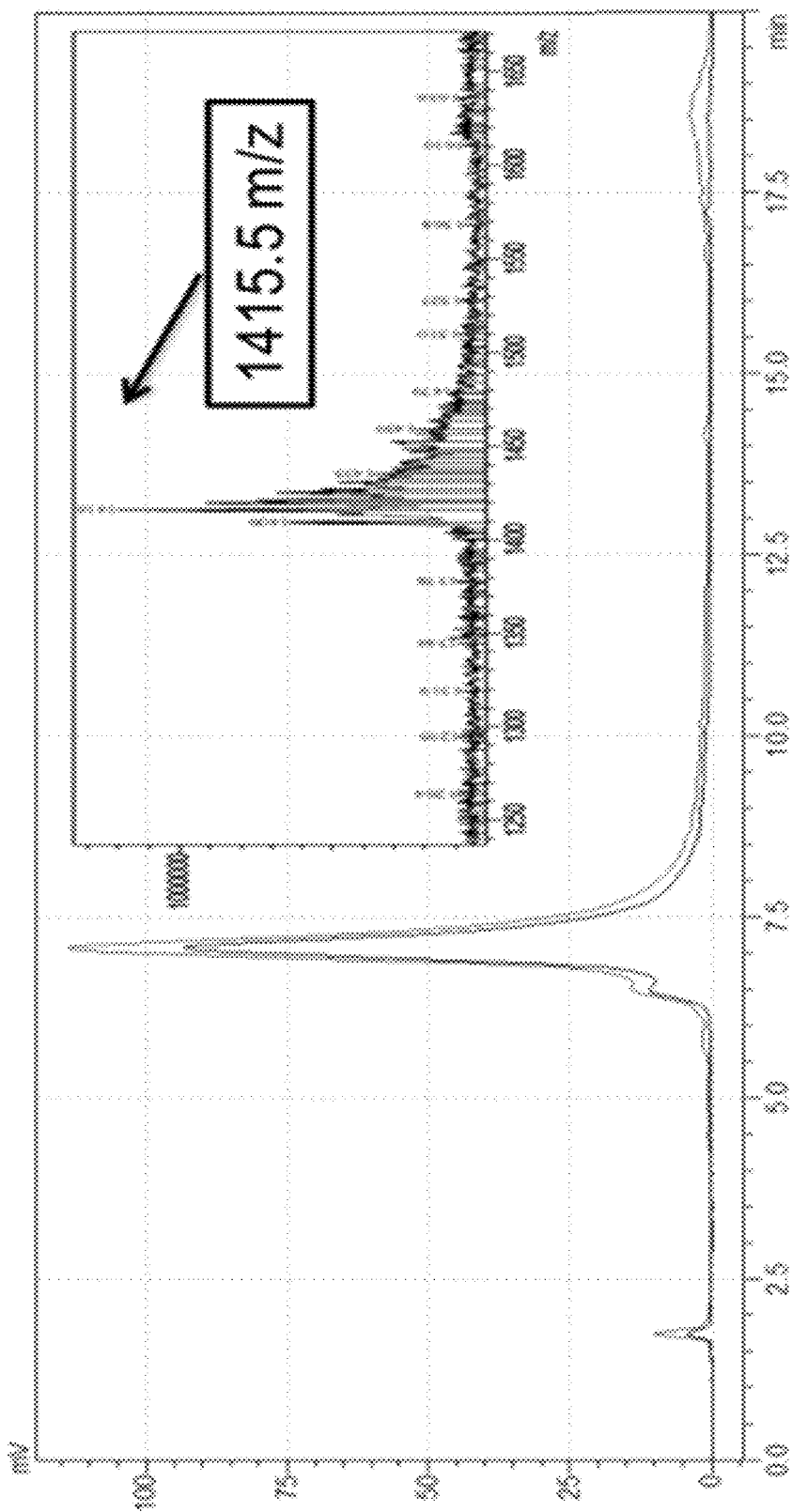
FIG. 2 depicts an LC trace showing purified compound 7 as a monomer (7.5 min) and dimer (6.5 min) and ESI MS (inset) of compound 7 showing m/z of 1415.5 Da, which corresponds to the +4 of compound 7 yielding a consistent mass of 5658 Da.

As seen in FIG. 2, compounds 6-9 were separated from compound 1 and unreacted $B_{12}$ on a C18 column monitored at both 280 and 360 nm. A mobile phase of 0.1% TFA water was used with a flow rate of 1 mL/min and a gradient from 20-42.5% acetonitrile for 3 min then 42.5-47% acetonitrile for 12 min. Isolated conjugates 6-9 were confirmed by electrospray mass spectrometry (ESMS) with that of compound 7 shown as representative in inset in FIG. 2. Note that the small shoulder on the front side of the LC trace was also found to be consistent with the target conjugate (compounds 6-9) and is consistent with the known tendency of Ex-4 to partially aggregate.

Example 3. Binding and Function of Compounds 1 and 6-9 Against GLP-1R

Figure 3:
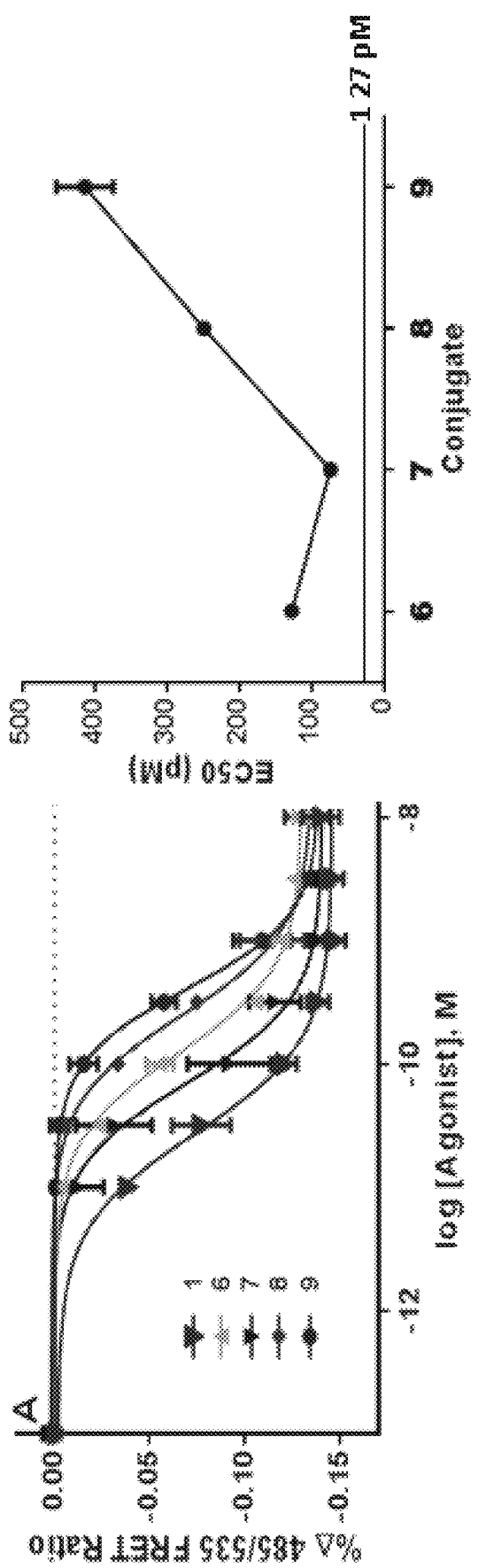
FIG. 3 depicts in panel A a graph of the EC50 curves for compounds 1, 6, 7, 8, and 9 and the second panel depicts a plot of the EC50 values for compounds 1, 6, 7, 8, and 9 (27, 121, 68, 246 and 271 pM, respectively).

Synthesis of compounds 6-9 was achieved in high yield (>90%) with greater than 95% purity in each case. Each conjugate was analyzed for function at the GLP-1R using Hek-GLP-1R cells incorporating a genetically-encoded FRET reporter, AKAR3. Upon binding of the GLP-1R, cAMP production is up regulated, which in turn activates protein kinase (PKA). PKA phosphorylation of AKAR3 results in a decrease of 485/535 nm emission FRET ratio. FIG. 3A shows dose response curves and $EC_{50}$ comparison of compounds 6-9 with compound 1 as a control. The most potent conjugate compound 7 had an $EC_{50}$ of 68 pM followed by compounds 6, 8, and 9, which had $EC_{50}$'s of 121, 246 and 405 pM, respectively.

Figure 4:
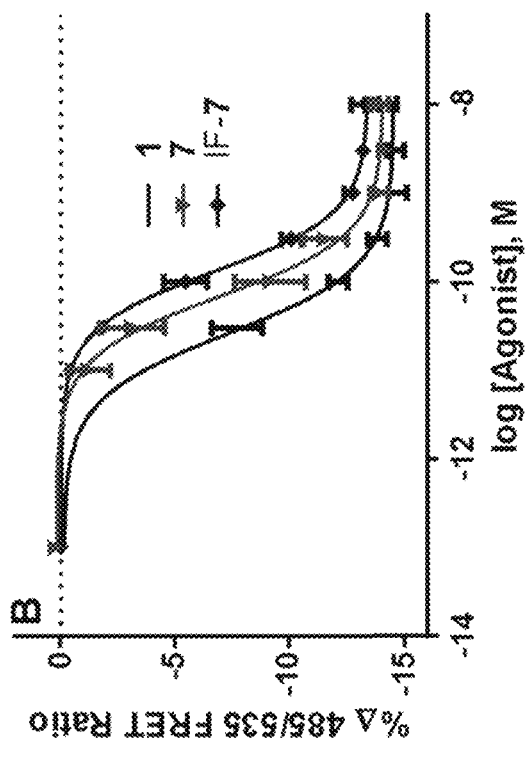
FIG. 4 depicts in panel A a graph of the binding affinities of the $B_{12}$ binding protein, IF, to compound 7 and to $B_{12}$ (as cyanocobalamin), namely 6.8 and 0.12 nM, respectively, and panel B depicts a graph of the $EC_{50}$ values for compound 7, IF-7 and compound 1, which were 68, 125, and 27 pM, respectively.
Figure 4:
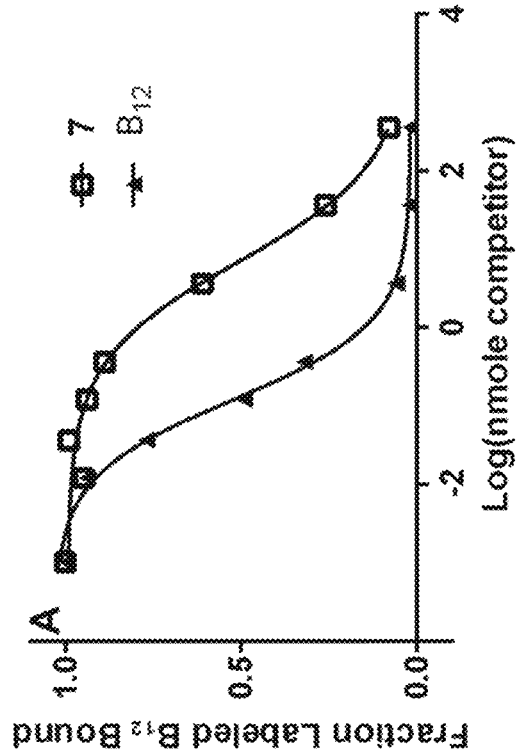

It appears from FIG. 3B there is a decidedly optimum spacer distance, with the shortest and longer distances resulting in reduced GLP-1R agonism. It is possible that interactions with the peptide, structural modification of the peptide or indeed interference with receptor interactions are all at-play (an NMR investigation study is-going and will be reported in due course). The data demonstrates the necessity of screening $B_{12}$ peptide conjugates prior to full in vivo investigations. With the in vitro data showing the most favorable response from compound 7, it was this conjugate that was subsequently used in in vivo studies. IF binding of compound 7 (producing IF-7) was compared to $B_{12}$ by doing a chase experiment with $^{57}Co$ radiolabeled $B_{12}$. FIG. 4A shows that compound 7 maintained significant IF binding (6.8 nM), albeit diminished compared to native $B_{12}$ (as cyanocobalamin; 0.12 nM).

Upon confirmation of binding to IF to produce IF-7, agonism of the GLP-1R was established. As indicated in FIG. 4B, IF-7 displayed significant agonism ($EC_{50}$ 125 pM) of the GLP-1R. This is indeed the first example confirming pre-binding of a $B_{12}$-peptide conjugate to a $B_{12}$ dietary protein (such as IF) maintains in vitro function (in this GLP1-R agonism) and is highly significant in its potential applications to $B_{12}$ based drug development in general.

Example 4. Effects of 1, 7 and IF-7 on Glucose Tolerance in Male Rats

The effect of compound 7 on glucose tolerance was measured to verify Ex-4 function in vivo was not disrupted by $B_{12}$ conjugation. An IPGTT (intraperitoneal glucose tolerance test) was done in male Sprague Dawley rats. The rats were administered saline (negative control and test vehicle), compound 1, compound 7, or IF-7 an hour prior to bolus glucose administration.

Figure 5:
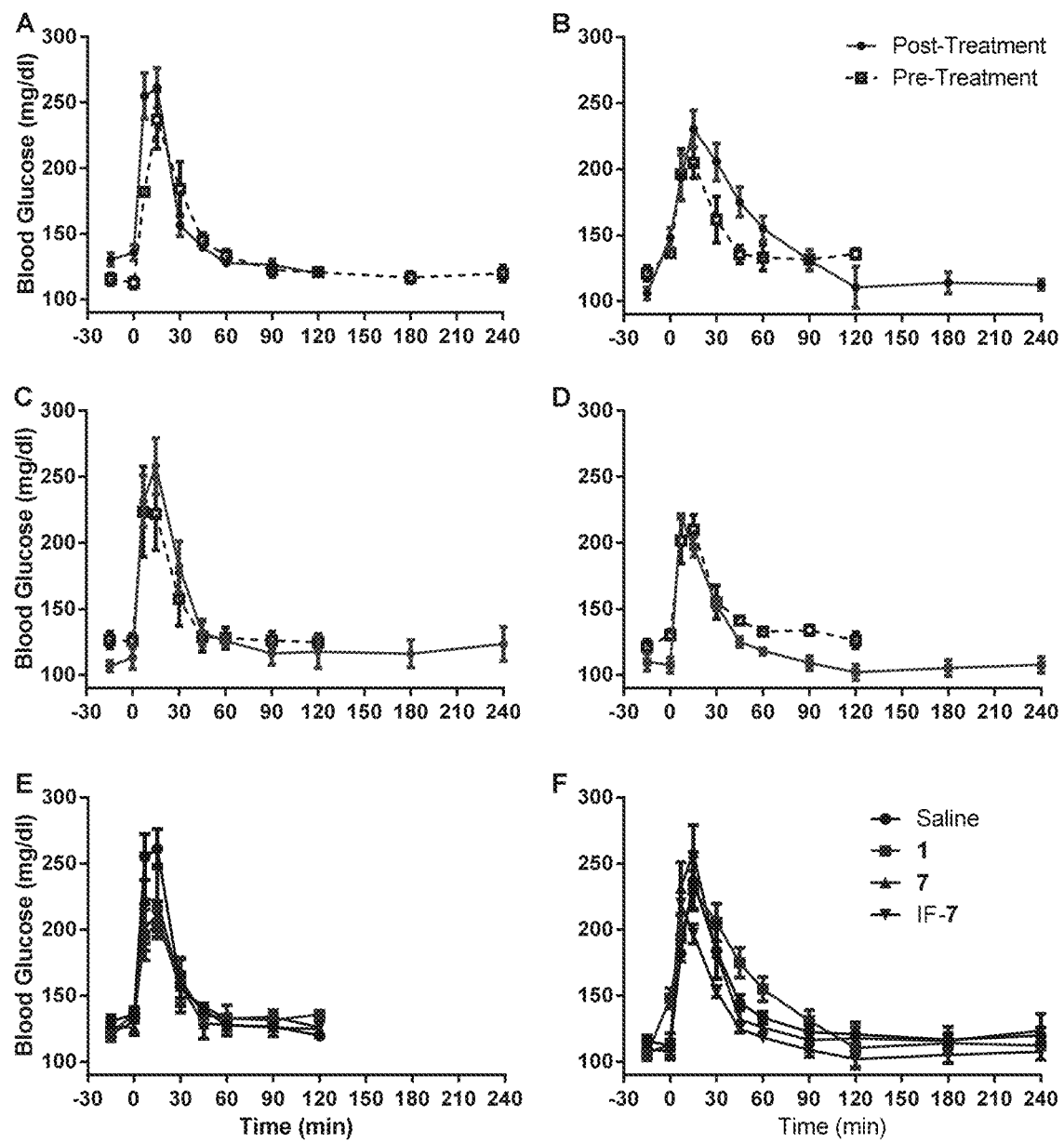
FIG. 5 depicts a series of graphs of IPGTT after administration of: (panel A) saline, (panel B) compound 1, (panel C) compound 7, (panel D) IF-7 at T=−15 min, where an overlay of pre-treatment data is shown in (panel E) and overlay of data post-treatment is shown in (panel F).

As seen in FIG. 5, the IPGTT showed that saline had no function and compound 1 showed an initial hyperglycemic response consistent with that reported in the literature and attributed to SNS activation. Glucose levels were noted to subsequently drop below baseline levels at ~90 minutes. As a surprise, especially given the improvement in function observed in our studies with $B_{12}$-PYY3-36, compound 7 showed no function in vivo, essentially modeling the saline negative control. A likely cause of the loss of GLP-1R agonism might be serum binding of TCII with subsequent rapid (within minutes) removal of the conjugate into proliferating cells systemically. In other words, at the doses administered for compound 7, the conjugate is behaving not as Ex-4, but rather as $B_{12}$.

From literature reports, saturation of TCII, even with large excesses of free $B_{12}$, proved difficult, so pre-binding 7 to IF was investigated in an attempt to prevent, at least initially, TCII binding and to explore the fundamental question of what effect IF binding would have on sc administration (a question not explored to date). Unlike TCII, IF does not occur naturally in blood serum and has no known cellular receptor (although recognition by cubilin found in the kidney is possible and has been shown ex-vivo by Christensen et al.). Upon IPGTT with IF-7 it can be immediately observed that, rather than the initial hyperglycemic response noted in rats for Ex-4, there is instead a drop in glucose levels, with levels dropping below baseline within 45 minutes and staying below out to 240 minutes. These results, conducted with an n of three over five separate IPGTT challenges indicate that binding of non-functional compound 7, does indeed confirm function, but highly interestingly, not that of unmodified Ex-4 in rats. Indeed, the drop in glucose levels with hyperglycemia is more typical of Ex-4 behavior in humans.

The present invention demonstrates that a series of $B_{12}$-Exendin-4 conjugates with potent agonism of the GLP-1R can be synthesized in high yield, and high purity. Azido modified K12 Ex-4 displays comparable agonism of the GLP-1R to unmodified Ex-4, which is key to the facile syntheses described. A four conjugate QSAR study indicated that distance between $B_{12}$ and Ex-4 was an important parameter in maintaining Ex-4 agonism of GLP-1R. An optimized conjugate was selected for IPGTT screening in vivo and investigated, both as free conjugate and bound to gastric IF protein. Of great significance was the fact that the free conjugate displayed no activity in vivo, despite potent agonism observed in vitro, yet the IF bound conjugate displayed a rapid and significant drop in glucose levels, critically without any hyperglycemia (implying no SNS activation in the rat model).

Example 5. Mitigation of Nausea

Conjugation of B12 to exendin-4 may also modify brain uptake or localization with the effect of reducing Ex-4 activity in the brain. Such a result would likely lead to a loss of the nausea seen with Ex-4, while still allowing hypoglycemic function through action at the pancreas for example. Nausea is a common side effect of such incretin hormone use and, as such, any maintaining of glucose control that also mitigates this nausea would have considerable benefit.

Materials and Methods for the Examples

Peptides were purchased through CSBio (Menlo Park, Calif.) and all materials were purchased through Sigma-Aldrich unless stated otherwise. Apo-IF was supplied by Xeragenx LLC (cat no: XGX-003). A Shimadzu Prominence with an automated fraction collector and dual wavelength detector was used for reverse phase high performance liquid chromatography (RP-HPLC) purification of samples. All chromatography was done with an Eclipse XDB C18 5 μm 4.6 mm×150 mm unless otherwise specified. Mass spectrometry was performed on a Bruker Autoflex III Matrix-Assisted Laser Desorption/Ionization Time of Flight Mass Spectrometer (MALDI-ToF MS). $^1$H NMRs were taken using a Bruker Advance DPX 400 MHz instrument. All fast protein liquid chromatography (FPLC) was done using a GE ÄKTAprime plus. IF used in these assays was produced in the plant *Arabidopsis* in the apo-form and of high purity All work done with HEK-GLP-1R cells was done at Upstate Medical University. Fluorescence intensity readouts were done using a FlexStation 3. Cells were grown in Celltreat 100 mm tissue culture dishes with DMEM+Glutamax-I with 4.5 g/L D-glucose, 110 mg/L sodium pyruvate, and 0.1% Geneticin (Life Technologies). About 60,000 cells were plated in each well of a 96 well plate.

Determining an Extinction Coefficient for Compounds 6-9 for Accurate Solution Concentration Measurement.

Once purified conjugate was produced, samples were quantified using amino acid analysis (AAA) at the Proteomics Core Facility at UC, Davis. The exact concentration obtained (data not shown) was then compared to an electronic absorption spectroscopy measurements (280 nm) of the exact samples taken prior to AAA and used to determine the extinction coefficient for compounds 6-9 of 20,300±3, 600 $M^{-1}$ $cm^{-1}$.

In Vitro Agonism at the GLP-1R by Compounds 6-9.

HEK cells stably transfected with human GLP-1R (HEK-GLP-1R) were used to test the potency of each new conjugate. The HEK-GLP-1R cells were grown in DMEM with 10% fetal bovine serum (FBS), 1% pen-strep and 0.1% geneticin all produced by Gibco. Cells were incubated at 37° C. in a humidified incubator with 5% $CO_2$. Cells were plated at 60,000 cells per well on a 96 well plate coated with rat tail collagen and incubated for 24 h. Media was then removed from the cells and DMEM containing 1% FBS and adenovirus incorporating A protein kinase reporter 3 (AKAR3) with an MOI per cell of 25 was added to each well. After 20 h of incubation the media was removed and 200 μL of standard extracellular solution (SES) was added to each well. Another 50 μL of SES containing conjugate was added to each well and immediately measured at 485 and 535 nm.

Binding to $B_{12}$ Binding Proteins.

Intrinsic factor and Transcobalamin II binding of compound 7 was confirmed using a $^{57}$Co radioassay.

What is claimed is:

1. A method of lowering blood glucose in a subject in need thereof, wherein the method comprises subcutaneously or intraperitoneally administering to the subject an effective amount of a pharmaceutical composition comprising intrinsic factor (IF) complexed with a conjugate comprising $B_{12}$ or an analog thereof conjugated to a peptide comprising a glucagon-like peptide-1 (GLP-1) receptor agonist.

2. The method of claim 1, wherein the lowering of blood glucose activity is increased relative to the lowering of blood glucose activity with the conjugate alone.

3. The method of claim 1, wherein the pharmaceutical composition further comprises one or more pharmaceutically acceptable diluents, excipients, and/or carriers.

4. The method of claim 1, wherein the peptide is conjugated to $B_{12}$ at the 5' hydroxyl residue of the ribosyl group.

5. The method of claim 4, wherein the 5'-hydroxyl residue of the ribose group is oxidized to a carboxylic acid prior to conjugation to the peptide.

6. The method of claim 1, wherein the $B_{12}$ or analog thereof is conjugated to the peptide via a linker.

7. The method of claim 6, wherein the linker comprises between three and six carbon atoms.

8. The method of claim 6, wherein the linker comprises 4 carbon atoms.

9. The method of claim 1, wherein the peptide comprises exendin-4 (EX-4).

10. The method of claim 1, wherein the peptide comprises the sequence set forth in SEQ ID NO:1 or SEQ ID NO:2.

11. The method of claim 10, wherein the peptide comprising SEQ ID NO:1 is conjugated to the 5'-hydroxyl residue of the ribose group of $B_{12}$ via the azido group at lysine 12 of SEQ ID NO:1.

12. The method of claim 1, wherein the IF is purified from a transgenic plant.

* * * * *